(12) United States Patent
Torres et al.

(10) Patent No.: US 8,636,795 B2
(45) Date of Patent: Jan. 28, 2014

(54) DEVICE TO STORE AND INJECT CORNEAL GRAFT

(75) Inventors: Aurora A. Torres, San Diego, CA (US); David J. Schanzlin, La Jolla, CA (US); Thomas A. Trozera, Del Mar, CA (US)

(73) Assignees: The Regents of the University of California, Oakland, CA (US); TDAK Medical Inc., San Diego, CA (US)

(*) Notice: Subject to any disclaimer, the term of this patent is extended or adjusted under 35 U.S.C. 154(b) by 527 days.

(21) Appl. No.: 12/429,080

(22) Filed: Apr. 23, 2009

(65) Prior Publication Data
US 2009/0270982 A1 Oct. 29, 2009

Related U.S. Application Data

(60) Provisional application No. 61/048,022, filed on Apr. 25, 2008.

(51) Int. Cl.
*A61F 2/14* (2006.01)

(52) U.S. Cl.
USPC .......................................................... 623/5.11

(58) Field of Classification Search
USPC ............... 606/107, 166; 623/6.12, 5.11, 6.38, 623/6.43
See application file for complete search history.

(56) References Cited

U.S. PATENT DOCUMENTS

| | | | | |
|---|---|---|---|---|
| 5,190,552 | A * | 3/1993 | Kelman | 606/107 |
| 5,667,489 | A * | 9/1997 | Kraff et al. | 604/22 |
| 6,605,093 | B1 * | 8/2003 | Blake | 606/107 |
| 6,858,033 | B2 | 2/2005 | Kobayashi | |
| 2005/0261703 | A1 * | 11/2005 | Feingold et al. | 606/107 |
| 2006/0020259 | A1 * | 1/2006 | Baumeister et al. | 606/5 |
| 2006/0173539 | A1 * | 8/2006 | Shiuey | 623/5.11 |
| 2006/0184181 | A1 * | 8/2006 | Cole et al. | 606/107 |
| 2007/0050023 | A1 * | 3/2007 | Bessiere et al. | 623/6.12 |
| 2007/0208422 | A1 | 9/2007 | Walter et al. | |
| 2007/0244559 | A1 | 10/2007 | Shiuey | |
| 2008/0243156 | A1 | 10/2008 | John | |
| 2008/0255578 | A1 | 10/2008 | Neusidl | |
| 2008/0269769 | A1 | 10/2008 | Dybbs | |
| 2008/0269771 | A1 | 10/2008 | Fulcher | |

(Continued)

FOREIGN PATENT DOCUMENTS

EP 1 424 047 A2 6/2004
WO WO 2007/035621 A1 3/2007

OTHER PUBLICATIONS

Berger, K. et al. "Corneal Membrane Transplant Injector SBIR Grant Proposal", Apr. 13, 2007, 11 pages.

(Continued)

*Primary Examiner* — S. Thomas Hughes
*Assistant Examiner* — Tin Nguyen
(74) *Attorney, Agent, or Firm* — Cooley LLP

(57) ABSTRACT

Devices and methods for storing and injecting a corneal tissue graft are disclosed herein. In one embodiment, an apparatus includes a tissue container and an adaptor configured to be coupled to the tissue container. The tissue container defines an interior region configured to receive a precut corneal tissue graft therein. The tissue container is also configured to be coupled to an injector assembly that can be used to move the corneal tissue graft out of the interior region of the tissue container and into an anterior chamber of a recipient's eye. The adaptor can be configured to prevent the tissue graft from migrating out of the tissue container and/or can be configured to be coupled to the injector assembly. The tissue graft can remain within the tissue container during storage, transport and during the implantation procedure until it is injected into the patient's eye.

36 Claims, 10 Drawing Sheets

(56) References Cited

U.S. PATENT DOCUMENTS

2008/0281341 A1   11/2008   Miller et al.

OTHER PUBLICATIONS

EndoShield™ *DSEK Graft Injection System*™ Information Sheet; 1 page.
International Search Report and Written Opinion for International Patent Application No. PCT/US09/41571, mailed on Dec. 2, 2009; 10 pages.
English Translation of Office Action cover pages for Chinese Patent Application No. 200980124697.0, mailed Sep. 26, 2012.
English Translation of Office Action cover pages for Chinese Patent Application No. 200980124697.0, mailed May 22, 2013.
Harvey, MD, "Corneal/Anterior Segment Surgery," Cornea Day 2008, Apr. 4, 2008.
Kaiserman, MD, MSC, MHA, "The elusive big bubble: is this the future of deep anterior lamellar keratoplasty?" Expert Rev. Ophthalmol. 4(1), 1-3 (2009).

* cited by examiner

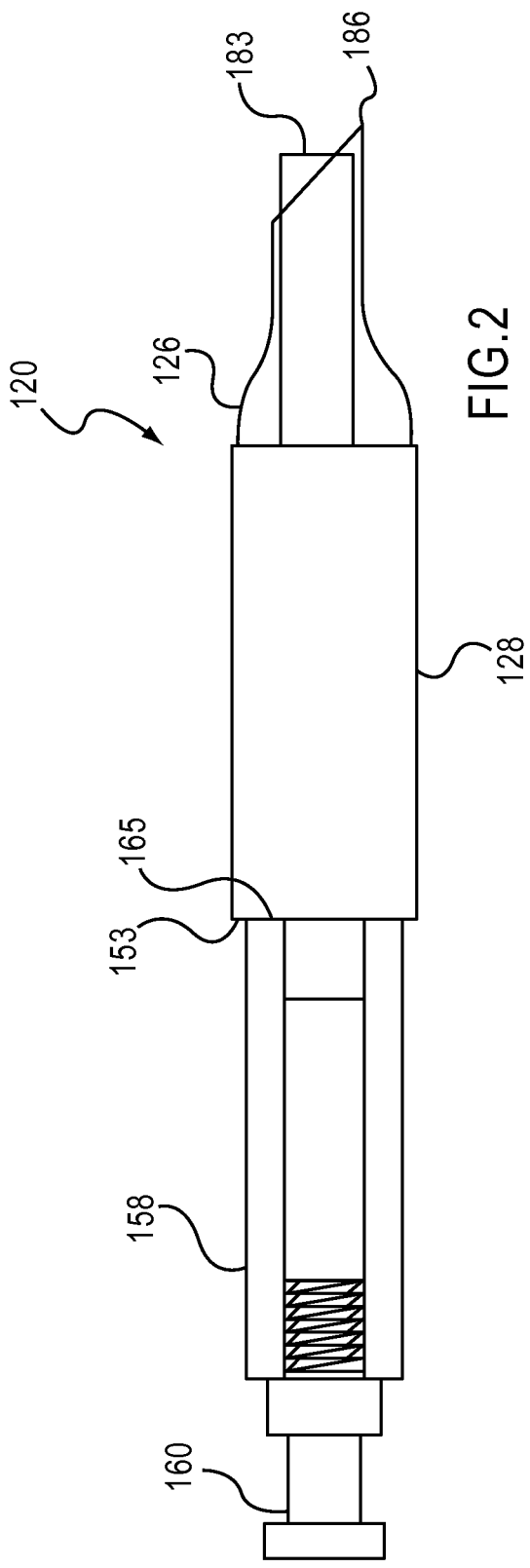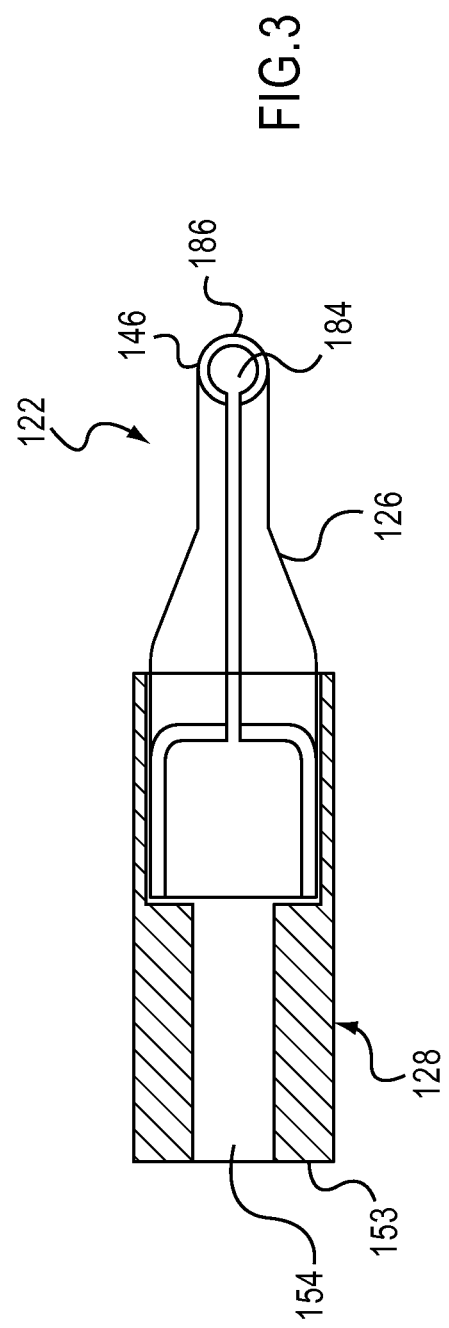

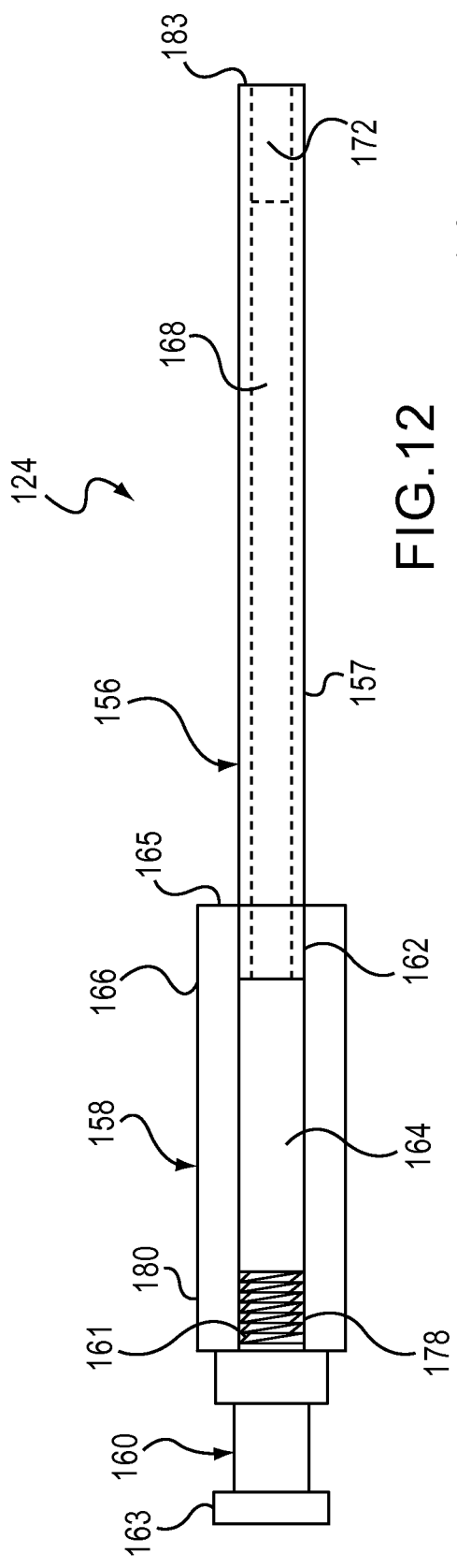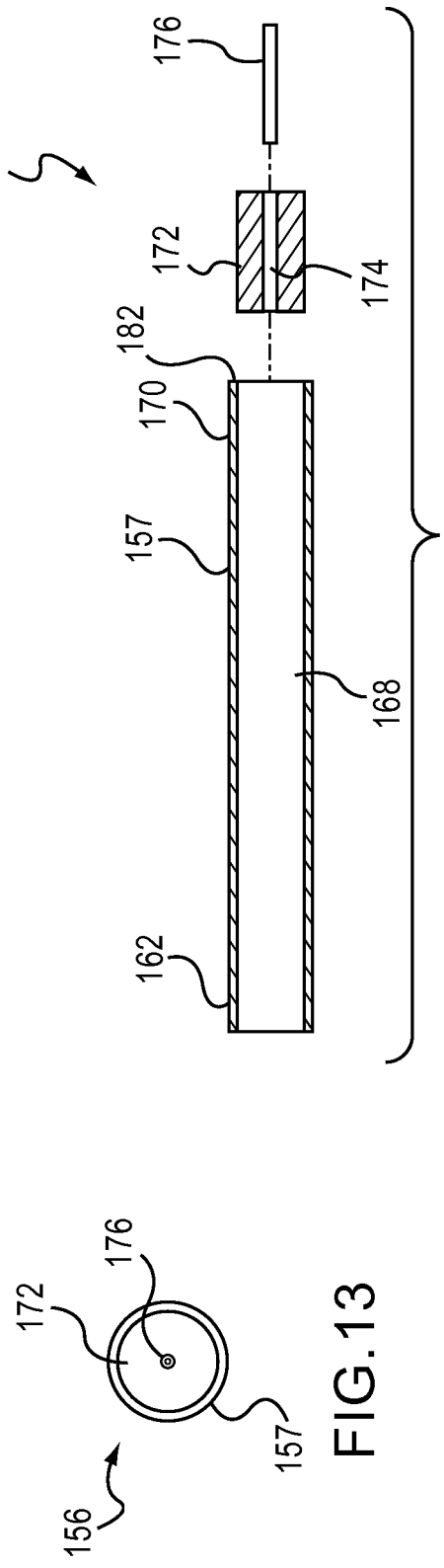

DEVICE TO STORE AND INJECT CORNEAL GRAFT

CROSS-REFERENCE TO RELATED APPLICATIONS

This application claims priority to U.S. Provisional Patent Application Ser. No. 61/048,022, entitled "Device To Store and Inject Corneal Graft," filed Apr. 25, 2008, the disclosure of which is hereby incorporated by reference in its entirety.

BACKGROUND

The invention relates generally to medical devices and procedures, including, for example, medical devices and methods for storing and injecting a corneal tissue graft.

Corneal transplantation is a widely practiced ophthalmic surgical procedure where the cornea from a donor is used to replace a scarred or diseased cornea of a patient to restore vision. Such corneal implants are performed to treat a variety of blinding diseases. Some of the most common corneal conditions that necessitate corneal transplantation include: Corneal Edema, Corneal Dystrophies, Keratoconus, and other conditions that lead to corneal scarring. Many corneal transplants are necessitated by corneal edema. Corneal edema, or swelling, can sometimes occur after cataract surgery or due to diseases such as Fuchs' dystrophy (i.e., an accumulation of focal excrescences called guttae and thickening of Descement's membrane, leading to corneal edema and loss of vision). Left untreated, the corneal swelling can cause blurred or foggy vision and can advance to a point such that tiny blisters form on the surface of the cornea. This condition results due to disease of the corneal endothelium, which is a single monolayer of specialized cells that line the back of the cornea.

Until recently, the management of corneal edema secondary to diseased corneal endothelium was with a penetrating keratoplasty (PK) procedure. A PK procedure is a surgical procedure where a full thickness corneal button replaces a full thickness button of the patient's cornea. Specifically, all of the layers of the cornea are replaced. In a PK procedure the donor cornea is sutured into the patient's cornea using nylon sutures. While penetrating keratoplasty has been very successful in restoring a clear cornea and eliminating the symptoms of corneal edema, due to wound healing irregularities, as well as difficulty creating a donor corneal button that is the exact size of the recipient's corneal button, high degrees of corneal astigmatism frequently results. This can lead to a situation where the patient has a clear cornea, but is unable to see through it because of optical aberrations.

Another known procedure is referred to as endothelial keratoplasty, which differs from penetrating keratoplasty in that only the posterior layers of the cornea are transplanted to the donor eye. Although endothelial keratoplasty has grown more popular as a treatment of corneal edema caused by endothelial cell failure, there are known problems associated with endothelial keratoplasty. One known problem is the potential damage to the donor corneal epithelium caused by current techniques of folding the tissue and then pushing the folded tissue through the corneal wound using forceps. This procedure can cause a crush injury to the delicate endothelial cells of the donor transplant tissue. Additionally, to fold the donor tissue into the eye using known techniques, a relatively large incision (e.g., 6 mm) is typically necessary. The large incision must be sutured closed before the endothelial keratoplasty button (e.g. tissue graft) is unfolded, which may lead to endothelial cell loss.

One known technique for endothelial keratoplasty is referred to as deep lamellar endothelial keratoplasty (DLEK). In this technique a pocket is made within the cornea and diseased corneal endothelium is excised along with a layer of corneal stroma. Healthy lamellar corneal stromal endothelial tissue is then transplanted into the space left by the excised diseased tissue. Another known technique is called Descemet's stripping endothelial keratoplasty (DSEK) or Descemet's stripping automated endothelial keratoplasty (DSAEK). In this technique, a lamellar corneal stromal endothelial transplant graft is transplanted into an anterior chamber of a patient's eye. For example, a diseased corneal endothelium in a recipient's eye is stripped away with surgical instruments and then the lamellar corneal stromal endothelial transplant graft is inserted into the anterior chamber through a full thickness corneal incision. The graft can then be held in place against the stripped posterior corneal stromal surface by, for example, an air bubble until the graft is able to heal in position. In some cases, a suture or sutures can be used to secure the tissue graft placement.

In both DLEK and DSEK (and DSAEK), it would be advantageous to be able to insert a relatively large transplant atraumatically through a small corneal or scleral incision. A larger transplant has more corneal endothelial cells and should produce better results in the treatment of corneal endothelial diseases. As discussed above, in some known methods, however, the tissue graft is folded and/or is grasped with forceps, which can damage the tissue cells. Moreover, the transplant is typically severely compressed as it passes through the corneal incision. In such procedures, the delicate corneal endothelial cells of a transplant can be damaged or killed during the insertion process.

Corneal implants can be made of either synthetic materials (e.g. prostheses) or can be biological in origin (e.g. donor grafts). Like corneal transplant grafts for DSEK or DLEK, synthetic corneal implants (e.g. corneal inlay prostheses) are also very delicate. In many cases, these corneal inlays may be as thin as 30 to 40 microns, which makes them very easily torn by forceps. Thus, there is also a need for an improved method to place corneal inlays atraumatically through a small incision.

There are many different types of corneal implants that have been developed for the treatment of refractive error and disease. Because of limitations in the methods of creating corneal pockets, these implants have all been designed for placement in the cornea by creation of a corneal incision, which is either similar in size to the smallest dimension of the implant or larger. Recently, two methods of corneal pocket creation have been devised which can create a pocket with an external opening width that is less than the maximum internal width of the pocket. These two methods are pocket creation by the femtosecond laser and, of particular interest, cornea cutting, as described in US 2004/0243159 and 2004/0243160 the full disclosure of which is incorporated herein by reference.

One known delivery system used in DSAEK is the Moria Busin device, which is a glide spatula for the insertion of a donor lamellar button. It provides a "pull-through" technique and minimizes intraoperative manipulation of the graft and the possibility of endothelial cell loss, but still requires the surgeon to load the tissue graft. There are 5 steps in the Busin "pull-through" technique: (1) The Busin glide is loaded with the donor lamella, endothelial side up; (2) The donor lamella is then pulled into the glide opening; (3) The glide is then inverted and positioned at the entrance of a nasal clear-corneal tunnel. A forceps passes through a temoral paracentesis wound across the anterior chamber and grasps the donor lamella from the glide. An anterior chamber maintainer is placed at 12 o'clock position to reform the anterior chamber; (4) The donor lamella is pulled into the anterior chamber; and (5) The donor lamella is left to unfold spontaneously under continuous irrigation.

There are also known delivery systems for placement of intraocular lenses (IOLs) into the posterior chamber of a patient's eye through a small incision. Such delivery systems, however, are designed for small incision cataract surgery and are typically not well adapted for use as a delivery system for corneal implants through a small incision. For example, a typical intraocular lens implant may be 1 mm or greater in thickness, whereas the typical corneal transplant for DLEK or DSEK is between 0.1 to 0.15 mm in thickness. Moreover, as noted above, the thickness of a corneal inlay prosthesis may be as little as 30 to 40 microns. In addition, the size and shape of an IOL is typically different from that of a corneal transplant. An IOL is typically 12 mm to 13 mm in length and 5 mm to 6 mm wide, whereas a corneal transplant is typically circular in shape and has a diameter, for example, of 8 mm to 9 mm. In the case of a corneal prosthesis inlay, the diameter may range from 1 mm to 10 mm. Finally, IOL delivery systems are designed to greatly compress the IOL during the insertion process, which can either damage or destroy a living corneal transplant.

Intraocular lenses for cataract surgery have also been designed to be placed through a small incision, however, these small incision cataract surgery lenses cannot practically be used within a corneal pocket. Most small incision cataract surgery lens implants are typically too thick to be placed within a corneal pocket. For example the typical thickness of a cataract surgery lens implant is 1 mm or more, which is substantially thicker than the human cornea, which is usually between 0.5 mm to 0.6 mm. Some corneal implants that have been designed only have a thickness of about 0.05 mm. Moreover, the cataract surgery lens implants have haptics, which are extensions from the lens implant designed to keep the lens implant fixated within the capsular bag. Haptics are not present, and not necessary, for corneal implants. Finally, the cataract surgery lens implants are not designed to be biocompatible with the cornea and would not be tolerated as corneal implants. Thus, the delivery systems designed for small incision cataract surgery lens implants are not well adapted for use as a delivery system for small incision corneal implants.

Thus, a need exists for an apparatus and method for storing a corneal tissue graft in a pre-cut ready to use state for transport to a surgeon that allows the tissue graft to remain untouched by the medical practitioner upon receipt of the tissue graft and during the implantation procedure. There is also a need for an apparatus and method for corneal implantation that does not damage or destroy a living corneal tissue graft during storage, transport and the implantation process, while providing ease of transplant for the surgeon.

SUMMARY OF THE INVENTION

Devices and methods for storing and injecting a corneal tissue graft are disclosed herein. In one embodiment, an apparatus includes a tissue container and an adaptor configured to be coupled to the tissue container. The tissue container defines an interior region configured to receive a precut corneal tissue graft therein. The tissue container is also configured to be coupled to an injector assembly that can be used to move the corneal tissue graft out of the interior region of the tissue container and into an anterior chamber of a recipient's eye. The adaptor can be configured to prevent the tissue graft from migrating out of the tissue container and/or can be configured to be coupled to the injector assembly. The tissue graft can remain within the tissue container during storage, transport and during the implantation procedure until it is injected into the patient's eye.

BRIEF DESCRIPTION OF THE DRAWINGS

FIG. 2 is a side view of a medical device according to another embodiment.

FIG. 3 is a side view shown partially in cross-section of a tissue storage device of the medical device of FIG. 2.

FIG. 12 is a side view of an injector assembly of the medical device of FIG. 2.

FIG. 13 is a distal end view of a portion of the injector assembly of FIG. 12.

FIG. 14 is an exploded view shown partially in cross-section of a portion of the injector assembly of FIG. 12.

DETAILED DESCRIPTION

Figure 1:
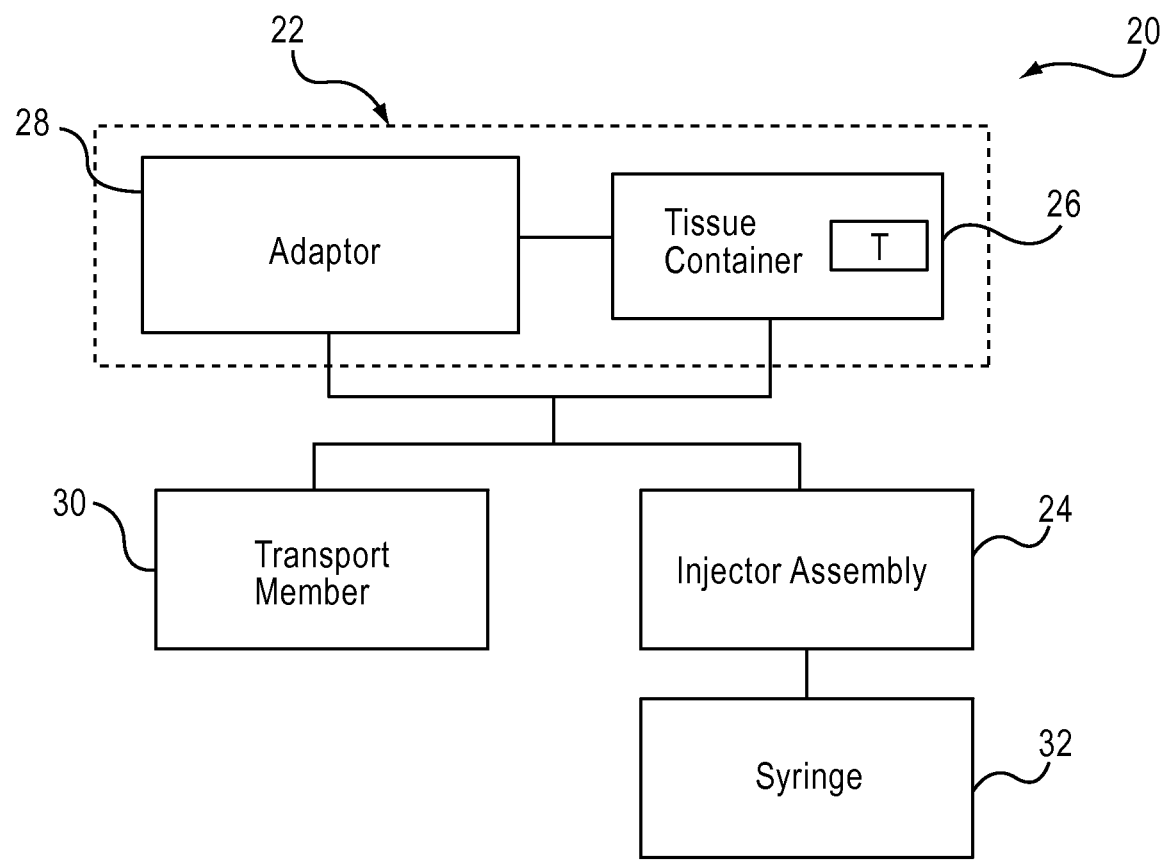
FIG. 1 is a schematic illustration of a medical device according to an embodiment.
Figure 4:
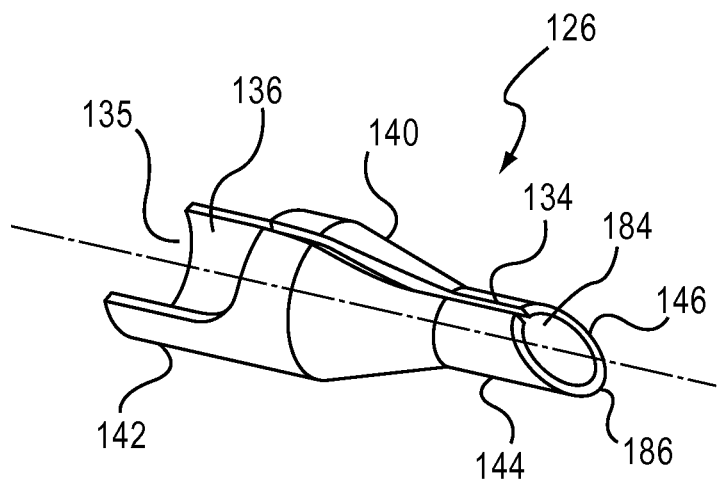
FIG. 4 is a side perspective view of a tissue container of the medical device of FIG. 2.
Figure 5:
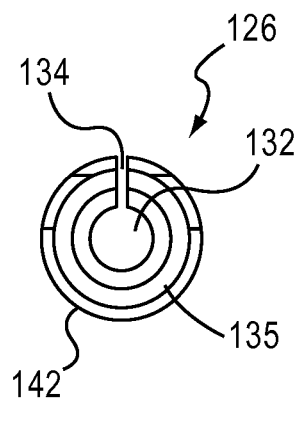
FIGS. 5 and 6 are a proximal end view and a distal end view, respectively, of the tissue container of FIG. 4.
Figure 6:
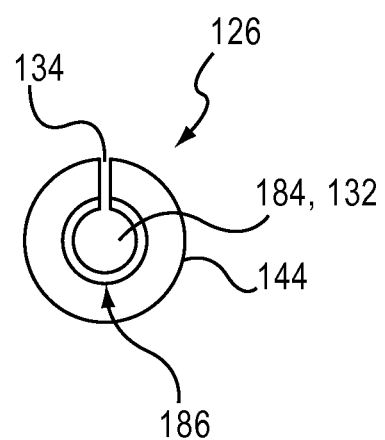
Figure 7:
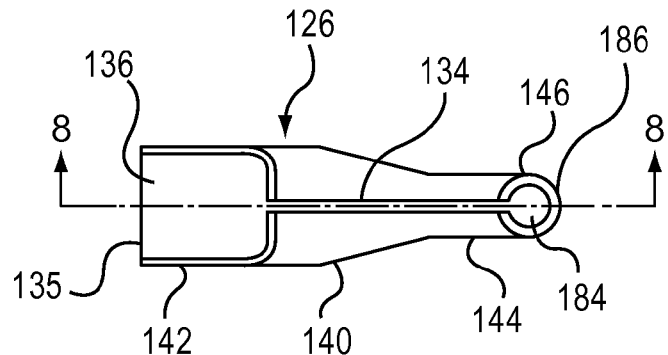
FIG. 7 is a top view of the tissue container of FIG. 4.
Figure 8:
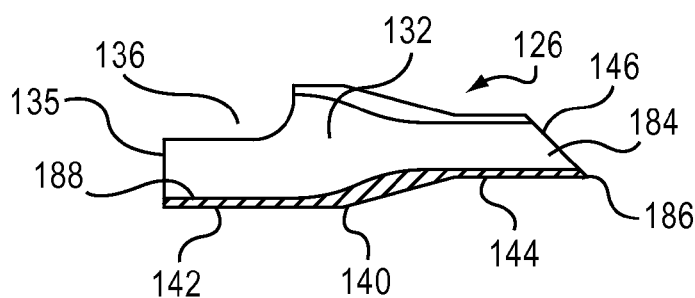
FIG. 8 is a cross-sectional view taken along line 8-8 in FIG. 7.

The devices and methods described herein are configured for use in the storage, transport and implantation of a corneal tissue graft. For example, a device (also referred to herein as "medical device" or "apparatus") can include a tissue container having an interior region for containing a precut corneal tissue graft. The tissue container can be configured to be coupled to an injector assembly that can be used to implant or inject the corneal tissue graft into an anterior chamber of a patient's eye. Thus, the tissue graft can remain disposed within the tissue container during storage, transport and the implantation procedure. Such a device can reduce or prevent damage to the tissue graft because the tissue graft does not have to be handled or manipulated by the surgeon. A device as described herein can also optionally include an adaptor configured to be coupled to the tissue container. In some embodiments, the adaptor can be used to prevent a corneal tissue graft from migrating out of the tissue container. In some embodiments, the adaptor can be coupled to an injector assembly used to inject the tissue graft into the anterior chamber of a patient's eye. As described herein, in some embodiments, all or some of the components can be included in a kit.

As discussed above, typical procedures currently used in corneal endothelial graft delivery in endothelial kerotoplasty include folding the graft (e.g., folding the graft in half) and the use of forceps to insert the graft through a small incision into the anterior chamber of the recipient eye. Such manipulation of the donor graft with forceps can cause damage to the fragile corneal endothelial cells. With the devices and methods described herein, a corneal tissue graft can be implanted into a recipient's eye with minimal or no graft endothelial manipulation as it is injected into the eye.

A device as described herein can be a single-use, disposable device that allows an ophthalmic surgeon to safely insert a previously prepared posterior donor cornea into the eye of a recipient patient, through a small incision during, for example, a posterior corneal transplant surgical procedure. The device can be inserted into a small corneal or scleral incision and then used to push the donor corneal tissue into the anterior chamber of the eye as part of an endothelial keratoplasty procedure.

In some embodiments, a device described herein can be used by, for example, an eye bank during the preparation and distribution of endothelial keratoplasty donor corneal tissue to the transplantation surgeon. In this usage, the prepared endothelial keratoplasty tissue can be loaded into a device, placed in a sterile corneal transplant tissue media and then packaged and shipped to the surgeon.

Thus, a device as described herein can be used to store a corneal graft, used in endothelial keratoplasty, such as Descemet's Stripping Endothelial Keratoplasty (DSEK), in a precut state, ready for injection through a small incision in a recipient's eye. The precut corneal graft can be preloaded into a chamber or interior region of the device prior to delivery to the surgeon and the device can include, or be coupled to, an injection device that can provide for easy injection of the tissue graft into the recipient's eye. This can advantageously minimize surgical time and the need for manipulation of the tissue graft by the surgeon during the procedure. Thus, the device can make the surgical procedure easier and convenient for the surgeon to insert the tissue graft into the patient's eye, since it eliminates certain steps in doing an endothelial keratoplasty surgery (e.g., DSEK), such as, for example, 1) the need to cut the tissue graft to a desired thickness and punch it with a trephine; 2) the need to separate the anterior from the posterior layer; and 3) folding the graft with a forceps prior to insertion at the time of the implantation procedure.

As described herein, in an endothelial keratoplasty procedure, such as a Descemet's Stripping Endothelial Keratoplasty (DSEK), a distal end of the device containing the tissue graft can, for example, be placed into a clear corneal or near clear corneal or scleral incision, and then the corneal tissue graft can be injected into the anterior chamber of the eye using an injection device. The entry incision in the eye can be, for example, between 2.8 mm and 3.2 mm, and the interior incision size can be, for example, between 3.2 and 3.4 mm. The incision can be made to allow for a self sealing corneal wound after the tissue graft is placed into the anterior chamber of the eye. Although a suture can be used to close the incision, a suture is not typically necessary.

In some embodiments, a device can include a tapered or funnel portion designed and structured to allow for the corneal tissue graft to be rolled and inserted into the interior region of the device effectively and safely, with minimal or no damage to the corneal endothelium. Rolling the tissue graft provides for less cellular damage than folding the tissue graft. In addition, rolling the tissue graft can allow the tissue to be inserted through a smaller opening in the scleral or corneal tissue. The device can also include a slot along at least a portion of its length to allow for irrigation of the tissue graft during storage and shipping. For example, the slot can allow for a nutritive substance, such as, Optisol, to pass easily into an interior region of the device where a tissue graft is contained. Exposing the tissue graft directly to the storage medium while the tissue graft is contained within the device can help maintain healthy metabolism in the cornea. The design and structure of the device can be used to deploy the tissue graft in a substantially controlled manner when it is gently pushed into the anterior chamber of a recipient's eye, thus, favorably reducing the risk of damaging the endothelial cells of the tissue graft.

As described above, some portions or all of a device can be provided in a sterile package and be disposable for single use to decrease the chance for contamination and infection. The device can also obviate the need for the surgeon to autoclave or use chemical sterilizers. For example, in some embodiments, the device (or a portion of the device) with a precut and preloaded corneal tissue graft contained therein can be placed within a transport member, such as a vial, containing a corneal storage medium, such as Optisol. This can further save substantial surgical time for the surgeon. Thus, the donor cornea tissue can be prepared, precut, and preloaded in the device in advance of a transplant procedure—even days prior to actual surgery—and placed in the corneal storage medium. For example, in some embodiments, a corneal tissue graft can be stored within a device as described herein for 72 hours. In some cases, a storage medium may preserve corneal endothelial cells for up to two weeks at, for example, 4° C., thereby permitting flexibility in the use of donor tissue for corneal transplantation.

The geometry and relative dimensions of the devices described herein may also minimize the potential for problems during release of the corneal tissue graft (also referred to as "button" or "disk") from the injection apparatus. For example, at least the portion of the device containing the tissue graft can have a smooth interior surface, which can reduce the possibility of an outer surface of the tissue graft from sticking to the inner walls of the device. In fact, the endothelium side of the graft should make no actual contact with the interior walls of the device when contained therein.

It is noted that, as used in this written description and the appended claims, the singular forms "a," "an" and "the" include plural referents unless the context clearly dictates otherwise. Thus, for example, the term "a lumen" is intended to mean a single lumen or a combination of lumens. Furthermore, the words "proximal" and "distal" refer to direction closer to and away from, respectively, an operator (e.g., surgeon, physician, nurse, technician, etc.) who would insert the medical device into the patient, with the tip-end (i.e., distal end) of the device inserted inside a patient's body. Thus, for example, the end inserted inside a patient's body would be the distal end of the medical device, while the end outside a patient's body would be the proximal end of the medical device.

FIG. 1 is a schematic illustration of an embodiment of a medical device. A medical device 20 can include a tissue storage device 22 and an injector assembly 24 (also referred to herein as "injection assembly" or "injector device" or "injection device"). A medical device 20 can also optionally include a syringe configured to be coupled to the injector assembly 24 and a transport member 30. Some or all of the above-described components can also be included in a kit.

The tissue storage device 22 can be a single component or include multiple components couplable together. For example, the tissue storage device 22 can include a tissue container 26 and an adaptor 28 that can be coupled to the tissue container 26. The adaptor 28 can be removably or fixedly coupled to the tissue container 26. For example, in some embodiments, the tissue container 26 and adaptor 28 are removably coupled with a slight friction fit. The transport member 30 can be for example, a vial, bag, or other suitable container defining an interior chamber sized and configured to contain a transplant storage medium (e.g., Optisol) and the tissue storage device 22. For example, the transport member 30 can be configured to contain a transplant storage medium, and (1) the tissue container 26, or (2) the tissue container 26 with the adaptor 28 coupled thereto.

The tissue container 26 can define an interior chamber or region (not shown in FIG. 1) configured to receive and contain a corneal tissue graft T, as described in more detail below. The interior region of the tissue container 26 can be sized such that a corneal tissue graft can remain disposed therein during storage and transport. The interior region of the tissue container 26 can also include substantially smooth interior walls such that friction between a tissue graft and the walls is minimized or eliminated.

The tissue container 26 can also include an elongated opening or slot (not shown in FIG. 1) defined along at least a portion of a length of the tissue container 26 and that is in fluid communication with the interior region of the tissue container 26. The slot can allow for a fluid, such as, a transplant storage medium (e.g., Optisol) to flow into the interior region and irrigate a tissue graft contained therein. The tissue container 26 can also define an opening (not shown in FIG. 1) defined in a side wall of the tissue container and in fluid communication with the interior region of the tissue container 26. The side opening can be used to insert a corneal tissue graft into the tissue container as described in more detail below with reference to specific embodiments. The tissue container 26 can also have an angled distal end portion to facilitate insertion into the recipient's eye, and a distal end exit opening in fluid communication with the interior region of the tissue container 26. In some embodiments, the elongated opening or slot along the length of the tissue container 26 extends to the distal end of the tissue container 26.

The tissue container can also include a tapered portion (not shown in FIG. 1). The tapered portion can be used to induce a corneal tissue graft into a rolled configuration within the tissue container 26. In some embodiments, the tissue container 26 includes a cylindrical distal end portion that has a substantially constant diameter, a proximal end portion, and a tapered portion disposed between the proximal end portion and the distal end portion. In such an embodiment, a tissue graft can be moved through the tapered portion and be stored and contained within the distal end portion while being stored and during transport to a surgeon. In some embodiments, the proximal end portion can include at least a portion that has a substantially constant diameter. The tissue container 26 can have a wall thickness that is substantially constant or can have varying wall thicknesses. For example, a distal end portion and/or a proximal end portion can have a thinner or greater wall thickness than a mid-portion or a tapered portion of the tissue container 26.

The adaptor 28 can be configured to prevent a corneal tissue graft from exiting or migrating out of the tissue container 26 and/or can be configured to be coupled to the injector assembly 24. In some embodiments, the adaptor 28 is used to couple the tissue container 26 to the injector assembly 24. In some embodiments, the adaptor 28 can include a distal portion defining an interior region (not shown in FIG. 1) configured to receive a proximal portion of the tissue container and a proximal portion defining a lumen (not shown in FIG. 1) configured to receive at least a portion of an injector assembly. In such an embodiment, when the adaptor 28 is coupled to the tissue container 26, the distal portion of the adaptor 28 can substantially cover a proximal portion of the tissue container 26. In some embodiments, when a tissue container 26 includes a side opening as described above, the distal portion of the adaptor 28 can close or cover the side opening of the tissue container 26.

The injector assembly 24 can be configured to be coupled to the tissue container 26 and/or the adaptor 28. The injector assembly 24 can include an injector arm or plunger (not shown in FIG. 1), and a housing (not shown in FIG. 1) as described in more detail below with reference to particular embodiments. The injector assembly 24 can be configured to be coupled to the tissue container 26 and/or adaptor 28 such that the plunger and the tissue container 26 and/or adaptor 28 can be moved relative to each other. For example, the plunger can be configured to be movably disposable within a lumen of the adaptor 28 and the interior region of the tissue container 26. The plunger can be used to move or inject a corneal tissue graft out of the tissue container 26 and into an intended recipient's eye.

The housing of the injector assembly 24 can be used to support the plunger and provide a surface for the surgeon to grasp during an endothelial keratoplasty procedure. The housing can define a lumen extending through at least a portion of a length of the housing. The plunger can be coupled to a distal end portion of the housing with, for example, a friction fit, a threaded coupling, an adhesive, or any combination thereof, or other known coupling methods. The plunger can be a variety of different shapes and cross-sectional configurations. For example, the plunger can be tubular and define a lumen through at least a portion of the plunger. The plunger can alternatively have a solid construction (i.e., no lumen). The plunger can have a circular cross-section or semi-circular cross-section or any of a variety of other cross-sectional configurations and can have a different cross-section at different locations along a length of the plunger. In some embodiments, the plunger is approximately 8 cm in length, but in alternative embodiments can be shorter or longer.

The injector assembly 24 can optionally include an irrigation channel (not shown in FIG. 1) and a coupling member (not shown in FIG. 1). The irrigation channel that can be configured to communicate fluid through the injector assembly 24 and to the corneal tissue graft and/or the recipient's eye. The coupling member can be coupled to a proximal portion of the housing or can be formed integrally or monolithically with the housing. The coupling member can be configured to releasably couple a fluid source 32, such as a syringe (e.g., a 1-3 cc syringe) or an IV line, to the injector assembly 24. The coupling member can be, for example, a luer lock coupler. The fluid source can be used to communicate a fluid, such as a saline solution, to the irrigation channel (not shown in FIG. 1) of the injector assembly 24. In some embodiments, the irrigation channel is defined by the plunger. For example, in some embodiments, the plunger includes an elongate cannula member (not shown in FIG. 1) that defines a lumen and a plug element (not shown in FIG. 1) that can be disposed within a distal end portion of the lumen. In some embodiments, the plug element can include a beveled proximal end to help prevent or eliminate accumulation of particulate material within the lumen of the elongate cannula member during the manufacturing process. For example, particulate material can be removed from the lumen of the elongate cannula member by blowing air into the lumen to loosen and remove the particulate matter. In some embodiments, the plug element can also include a beveled distal end. In some embodiments, the bevels on the distal end of the plug element can be filled with an adhesive or other suitable material, to create a small dome on the distal end of the plug element. The plug element can be, for example, adhesively bonded to interior walls of the elongate cannula member of the plunger and/or coupled thereto with a friction fit. A small gauge fluid port member (not shown in FIG. 1) can be disposed within a lumen of the plug element. The fluid port member can be tubular and formed with, for example, a 25 gauge stainless steel material. The fluid port member can be, for example, adhesively secured to the interior walls of the plug element and/or coupled thereto with a friction fit or other suitable coupling methods. In some embodiments, the lumen of the plug element varies in diameter (e.g., is tapered) along a length of the plug element to provide a smooth transition to the fluid port member and/or to prevent the forming of a ledge on the proximal end of the medical device 20 and the accumulation of particulate within the medical device 20. In alternative embodiments, a separate fluid port member is not included. Specific embodiments of an injector assembly and plunger are described in more detail below.

The medical device 20 can be used to store, transport and deliver a donor corneal tissue graft that can be a variety of different shapes and sizes. For example, a corneal tissue graft can be disk shaped, and can have, for example, a diameter of 8 mm or 9 mm. Other sizes of the tissue graft are also possible. For example a corneal tissue graft can be larger or smaller and can have different shapes, such as elliptical, oval, square, rectangular, etc.

Having described above various general examples, examples of specific embodiments are described below. These embodiments are only example, and many other configurations and uses of the devices described herein are contemplated.

FIGS. 2-14 illustrate a medical device 120 according to one embodiment. The medical device 120 includes a tissue storage device 122, and an injector assembly 124. FIG. 2 is a side view of the medical device 120 illustrating the tissue storage device 122 coupled to the injector assembly 124 and the injector assembly extended fully within the tissue storage container 122. As shown in FIG. 3, the tissue storage device 122 includes a tissue container 126 and an adaptor 128 (shown in cross-section) removably couplable to the tissue container 126 with, for example, a slight friction fit.

As shown in more detail in FIGS. 4-8, the tissue container 126 defines an interior region 132 configured to receive and contain a corneal tissue graft (not shown). The tissue container 126 also defines an elongated opening or slot 134 along a portion of a length of the tissue container 126 and in fluid communication with the interior region 132. As described above, the elongated opening 134 allows for a fluid, such as, a transplant storage medium (e.g., Optisol) to flow into the interior region 132 and irrigate a tissue graft contained therein when the adaptor 128 is coupled to the tissue container 126.

The tissue container 126 also defines a side opening 136 at a proximal portion 142 of the tissue container in fluid communication with the interior region 132 and an open proximal end 135. The side opening 136 can be used to insert a corneal tissue graft into the tissue container 126 as described in more detail below.

The tissue container 126 further includes a tapered or funnel portion 140 disposed between the proximal portion 142 and a cylindrical distal portion 144 of the tissue container 126. At least a portion of the distal portion 144 has a substantially constant outer diameter. An angled distal tip 146 portion defines a distal opening 184 of the tissue container 126. The angled distal tip portion 146 can help facilitate entry into the patient's eye.

Figure 9:
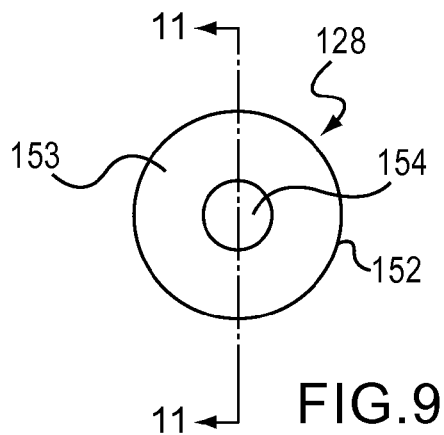
FIGS. 9 and 10 are a proximal end view and a distal end view, respectively, of an adaptor of the medical device of FIG. 2.
Figure 10:
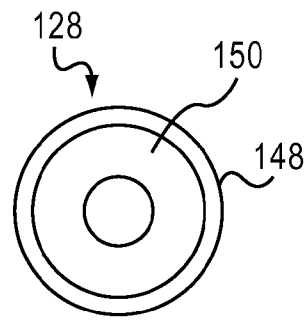
Figure 11:
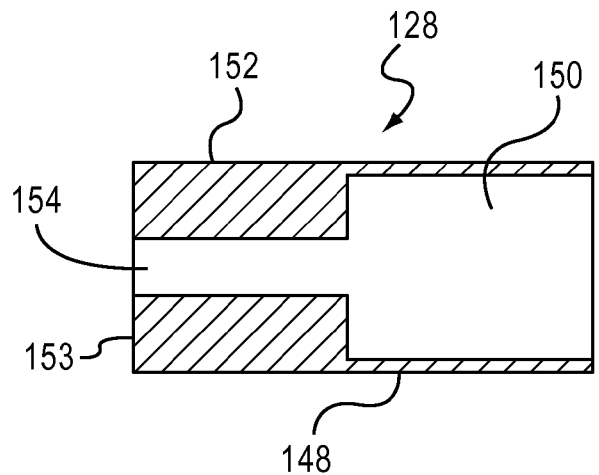
FIG. 11 is a cross-sectional view of the adaptor of FIGS. 9 and 10 taken along line 11-11 in FIG. 9.

FIGS. 9-11 illustrate the adaptor 128; FIGS. 9 and 10 are a proximal end view and a distal end view, respectively, and FIG. 11 is a cross-sectional view of the adaptor 128. The adaptor 128 includes a distal portion 148 defining an interior region 150 and a proximal portion 152 defining a lumen 154. The interior region 150 of the distal portion 148 is configured to receive the proximal portion 142 of the tissue container 126, and the lumen 154 of the proximal portion 152 is configured to receive an injector arm or plunger 156 of the injector assembly 124 (described below). In this embodiment, the proximal portion 152 includes a proximal end surface 153. In other embodiments, however, the proximal portion 152 of the adaptor 128 can be formed with internal ribs or strengthening members, rather than having a solid surface, such as proximal end surface 153. When the adaptor 128 is coupled to the tissue container 126, as shown in FIG. 3, the proximal portion 142 of the tissue container 126 is disposed within the interior region 150, and the side opening 136 is covered by the distal portion 148 of the adaptor 128.

The injector assembly 124 is illustrated in FIGS. 12-14. The injector assembly 124 can be removably coupled to the tissue storage device 122. The injector assembly 124 includes the plunger 156, a housing 158 and a coupling member 160. In this embodiment, the housing 158 defines a lumen 164 that extends between a proximal end and a distal end of the housing 158. The lumen 164 can have a constant diameter along its length or the diameter can vary. For example, a portion of the lumen 164 associated with a distal end portion of the housing 158 can have a smaller or larger diameter than a portion of the lumen 164 associated with a proximal end portion of the housing 158. A proximal end portion 162 of the plunger 156 is coupled to a distal end portion 166 of the housing 158. Specifically, in this embodiment, the proximal end portion 162 of the plunger 156 is disposed within the lumen 164 and is adhesively coupled to interior walls of the housing 158. It should be understand, however, that alternative coupling methods can be used, such as, for example, a threaded coupling.

As shown in the exploded view of FIG. 14, the plunger 156 includes an elongate member 157 that defines a lumen 168 extending between the proximal end portion 162 and a distal end portion 170 of the elongate member 157 of the plunger 156. The lumen 168 provides an irrigation channel to communicate fluid through the medical device 120. A plug element 172 is adhesively coupled to interior walls of the elongate member 157 within the lumen 168 at the distal end portion 170 of the elongate member 157 (see e.g. FIGS. 12 and 13). As discussed above, the plug element 172 can alternatively be coupled with a friction fit, a threaded attachment or other known coupling methods.

The plug element 172 can extend to a distal end 182 of the elongate member 157 or can extend just beyond the distal end 182. The plug element 172 can optionally have a beveled or domed distal end to help prevent accumulation of particulate on the distal end of the plunger 156. The plug element 172 also defines a lumen 174 configured to receive fluid port member 176. The fluid port member 176 can be, for example, adhesively secured to the interior walls of the plug element 172. The fluid port member 176 also defines a lumen that extends to a distal end of the plunger 156, as shown in FIG. 13. The fluid port member 176 can be used to communicate fluid into a patient's eye as described in more detail below.

In this embodiment, the coupling member 160 includes a threaded portion 161 that can be threadedly coupled to a mating threaded portion 178 defined within the lumen 164 of the housing 158 at a proximal end portion 180 of the housing 158. The coupling member 160 also includes a proximal portion 163 configured to releasably couple a fluid source (not shown), such as a syringe, to the injector assembly 124. The coupling member 160 in this embodiment can be, for example, a luer lock.

To couple the injector assembly 124 to the tissue storage device 122 (e.g., the tissue container 126 coupled to the adaptor 128), the plunger 156 is inserted into the lumen 154 of the adaptor 128. The plunger 156 can extend through the lumen 154 and into the interior region 136 of the tissue container 126. In some embodiments, the plunger 156 has a length such that when the injector assembly 124 is coupled to the tissue storage device 122 and extended fully within the tissue storage device 122, a distal end 183 of the plunger 156 does not extend beyond a distal most end 186 of the tissue container 126 (see e.g., FIG. 2), and the proximal end surface 153 of the adaptor 128 abuts a distal end surface 165 of the housing 158 (see e.g., FIG. 2). In some embodiments, the plunger 156 can have a length such that the distal end 183 of the plunger 156 can extend beyond the distal most end 186 of the tissue container 126. For example, in some embodiments, the distal end 183 of the plunger 156 can extend up to 1 mm beyond the distal most end 186 of the tissue container 126.

The plunger 156 has an outer diameter sized and configured to interface with the interior walls of the adaptor 128 (i.e., within the lumen 154) and the interior walls of the distal end portion 144 of the tissue container 126 (i.e., within the interior region 132), such that the plunger 156 can move smoothly therethrough. For example, in some embodiments, the plunger 156 can move within the tissue container 126 and adaptor 128 with, for example, between 25 and 100 grams of resistance. As discussed in more detail below, the plunger 156 can be used to push or move a corneal tissue graft (e.g., pre-loaded in a rolled configuration within the tissue container 126) into an anterior chamber of a patient's eye.

As discussed previously, the medical device 120 can be used to store, transport and deliver a donor corneal tissue graft into an anterior chamber of a recipient's eye. First, the tissue container 126, adaptor 128 and injector assembly 124 can be provided to an entity, such as an eye bank, that prepares corneal tissue grafts for storage and transport to a surgeon or other medical professional. The tissue container 126, adaptor 128 and injector assembly 124 can be provided separately or in a kit. In some embodiments, the tissue container 126 and adaptor 128 are provided separately from the injector assembly 124.

At an entity, such as an eye bank, corneal tissue is harvested, cut and viability stained. For example, a donor cornea, still with a scleral rim, can be cut with, for example, a microkeratome with a 300 or 360 micron head, and an anterior lamellar cap is removed from the posterior portion. The residual portion of the donor cornea can then be transferred, endothelial side up, to, for example, a Moria Hanna Punch Block and punched with a trephine blade. It should be understood that this is just one example of a procedure to prepare a corneal tissue graft as performed at an eye bank. Once the corneal tissue graft is ready for transplantation, the eye bank technician loads the corneal tissue graft into the tissue container 126.

Figure 15:
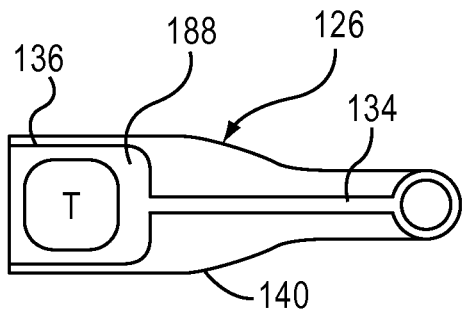
FIG. 15 is a top view of the tissue container of FIG. 4 shown with a schematic representation of a corneal tissue graft.
Figure 16:
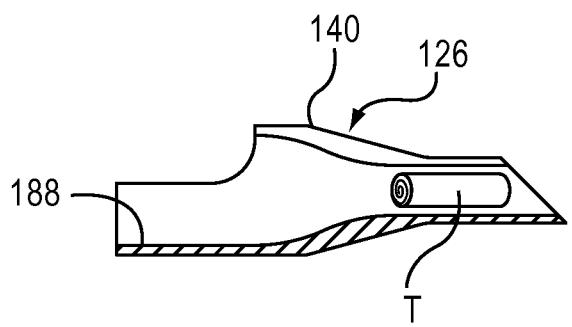
FIG. 16 is a side cross-sectional view of the tissue container of FIG. 4 shown with a schematic representation of a corneal tissue graft.

Specifically, using aseptic techniques, the technician removes the tissue container 126 and adaptor 128 from their package(s) and places them in a sterile field. Interior surfaces of the tissue container 126 and adaptor 128 can be pre-wet with a transplant medium, such as Optisol GS transplant media by Bausch and Lomb. As shown in FIG. 15, the tissue container 126 is oriented such that the elongated opening 134 is facing upward and a corneal tissue graft T (shown schematically) is placed with the endothelial cell side up through the side opening 136 and positioned on an interior surface 188 of the tissue container 126. Using a small forceps or similar medical tool to grab the stroma at the periphery of the cell tissue graft, the tissue graft T is moved through the tapered portion 140 and into the cylindrical distal portion 144 of the tissue container 126. The tapered portion 140 is configured to induce the tissue graft T to roll upon itself as it is moved therethrough, such that when the tissue graft T is positioned in the cylindrical distal portion 144 it is in a rolled configuration (see FIG. 16).

Figure 17:
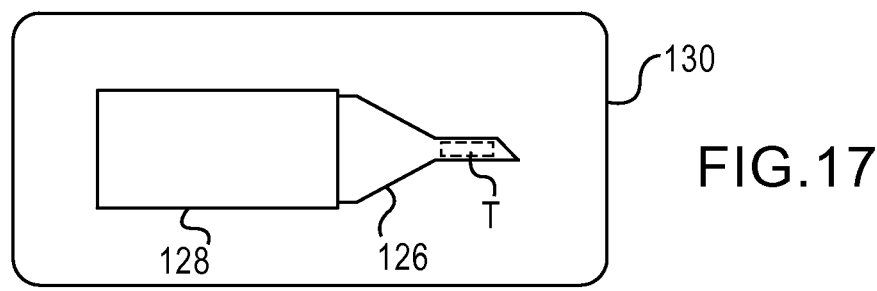
FIG. 17 is a side view of the tissue container and adaptor of FIG. 3 shown disposed within a transport member.

The adaptor 128 can then be coupled to the tissue container 126 (see e.g., FIG. 3). With the adaptor 128 coupled to the tissue container 126 (also referred to when coupled together as tissue storage device 122), the tissue storage device 122 can then be placed in a sterile transport member 130 (as shown in FIG. 17) containing a transplant storage medium such as, for example, Optisol. Identifying information, such as, for example, identifying the tissue and the date and time of loading the tissue can be recorded on a label and attached to the transplant member 130. The transplant member 130 can then be stored and/or transported to a surgeon. The tissue graft can typically remain stored within the transport member 130 for up to, for example, approximately 72 hours. In some embodiments, the original packaging that contained the tissue container 126 and adaptor 128 can be reused to send the transport member 130 to the surgeon. In some embodiments, that same packaging can also contain the injector assembly 124.

The surgeon receives the transport member 130 (containing the tissue storage device 122) and the injector assembly 124. The surgeon prepares the patient according to normal protocols for endothelial keratoplasty transplant surgery and makes a lateral incision at the scleral-corneal junction, facing away from the patient. The lateral incision can be, for example, approximately 3 mm-4 mm in length. In some embodiments, the incision can be approximately 3.5 mm in length. Using aseptic techniques, the surgeon removes the injector assembly 124 from its packaging and attaches a sterile syringe (e.g., a syringe 32 illustrated in FIG. 1) to the injector assembly 124 via the coupling member 160. The sterile syringe can be, for example, a 1 cc or 3 cc sterile syringe, filled with a balanced saline solution (BSS). The surgeon first flushes the irrigation channel 168 of the injector assembly 124 (e.g., with 0.3-1.0 cc of BSS). The surgeon can verify the tissue storage date and removes the tissue storage device 122 (i.e., tissue container 126 coupled to the adaptor 128 coupled thereto) from the transport member 130, and couples the injector assembly 124 thereto.

With the injector assembly 124 coupled to the tissue storage device 122, the surgeon can grasp, for example, the housing 158 or the adaptor 128 and orient the medical device 120 such that the elongated opening 134 on the tissue container 126 is facing posteriorly and then insert the distal tip 184 in the lateral incision at the corneal margin in the eye. The plunger 156 can then be actuated slowly (e.g., moved distally) to gently push or move the rolled corneal tissue graft T out the distal opening 184 of the tissue container 126 and into the anterior chamber of the eye. To help open or unroll the tissue graft T, BSS fluid inside the syringe can be injected through the medical device 120, out the fluid port member 176 and into the patient's eye.

Figure 18:
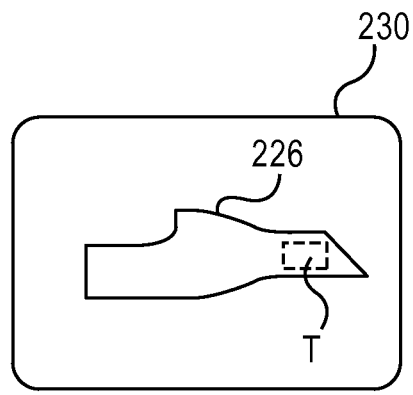
FIG. 18 is a top view of a medical device according to another embodiment.

FIG. 18 is an example of a medical device according to another embodiment. In this embodiment, a tissue container 226 is shown disposed within a transport member 230. Thus, in some embodiments, a tissue container, such as tissue container 226, can be provided to a surgeon with a corneal tissue graft T disposed therein without an adaptor (e.g., adaptor 28, 128). The tissue container 226 can be configured similarly as the previous tissue container 126 and the corneal tissue graft T can be inserted into the tissue container 226 in the same manner as described above for tissue container 126. Likewise, the transport member 230 can be configured as previously described.

Figure 19:
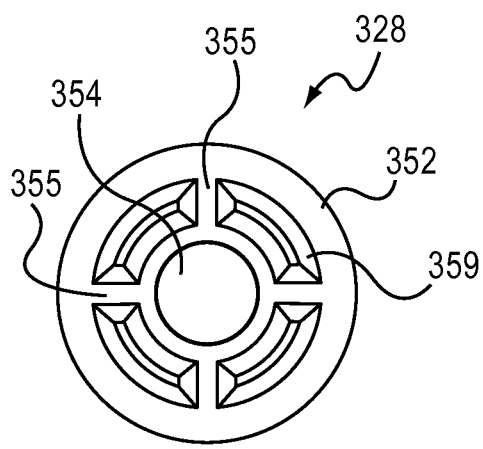
FIGS. 19 and 20 are a proximal end view and a distal end view, respectively, of an adaptor according to another embodiment.
Figure 20:
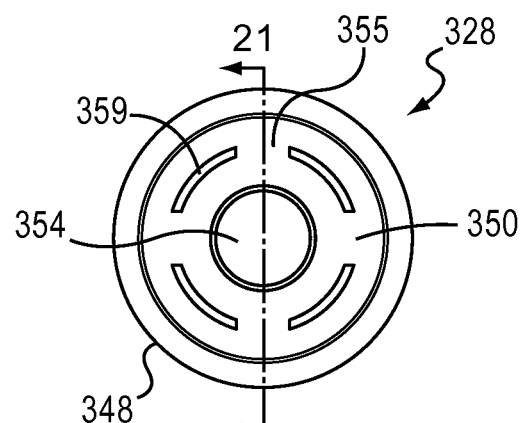
Figure 21:
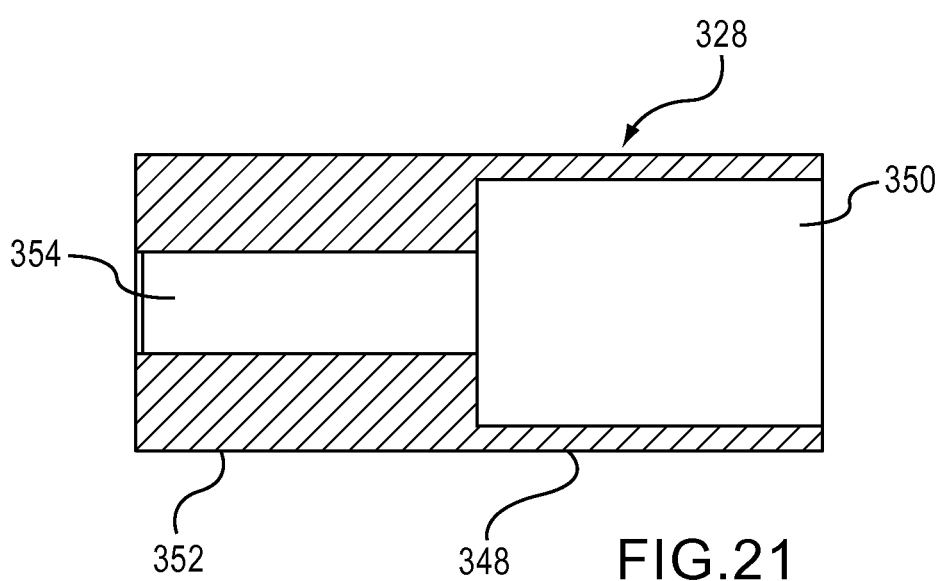
FIG. 21 is a cross-sectional view of the adaptor of FIGS. 19 and 20, taken along line 21-21 in FIG. 20.

FIGS. 19-21 illustrate another embodiment of an adaptor. An adaptor 328 includes a distal portion 348 defining an interior region 350 and a proximal portion 352 defining a lumen 354. As with the previous embodiments of an adaptor (e.g., 28, 128), the interior region 350 of the distal portion 348 can be configured to receive the proximal portion (e.g., 142) of a tissue container (e.g., 126), and the lumen 354 of the proximal portion 352 can be configured to receive an injector arm or plunger (e.g., 156) of an injector assembly (e.g., 124). In this embodiment, the proximal portion 352 includes internal webs or strengthening members 355 that define openings 359. The openings 359 taper towards the distal end such that in the distal end view (FIG. 20) the openings 359 are smaller in size that in the proximal end view (FIG. 19).

Figure 22:
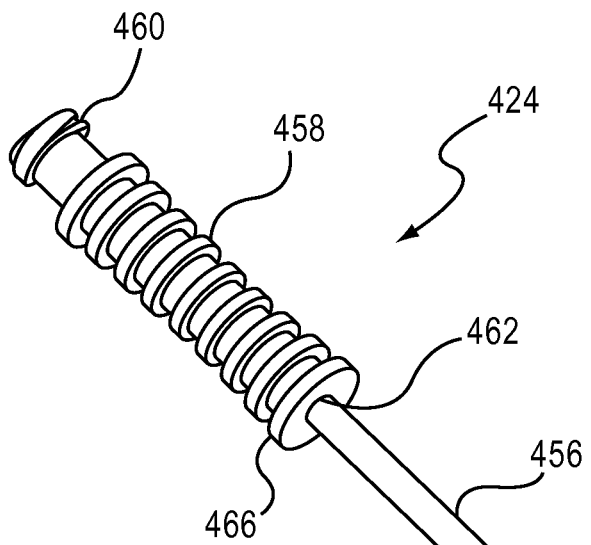
FIG. 22 is a perspective view of an injector assembly according to another embodiment.

FIG. 22 illustrates another embodiment of an injector assembly. An injector assembly 424 includes a plunger 456 and a housing 458. As with the previous embodiments, the housing 458 can define a lumen (not shown) that extends between a proximal end and a distal end of the housing 458. A proximal end portion 462 of the plunger 456 is coupled to a distal end portion 466 of the housing 458 in a similar manner as described above for injector assembly 124. The plunger 456 can be a solid construction, or be cannulated (e.g., define a lumen therethrough). In some embodiments, the plunger 456 can be constructed the same as the plunger 156 and include an irrigation channel, a plug element, and a fluid port member as described above.

In this embodiment, a coupling member 460 is integrally or monolithically formed with the housing 458. The coupling member 460 can be configured to releasably couple a fluid source (not shown), such as a syringe, to the injector assembly 424 and can include, for example, a luer lock.

Figure 23:
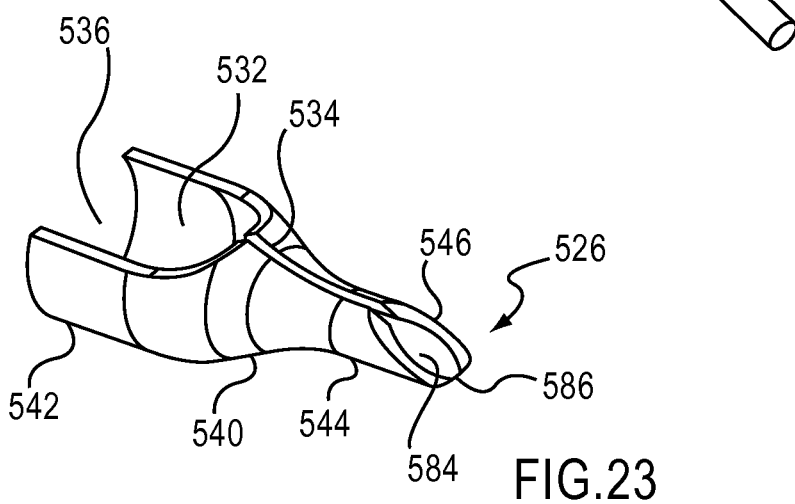
FIG. 23 is a side perspective view of a tissue container according to another embodiment.
Figure 24:
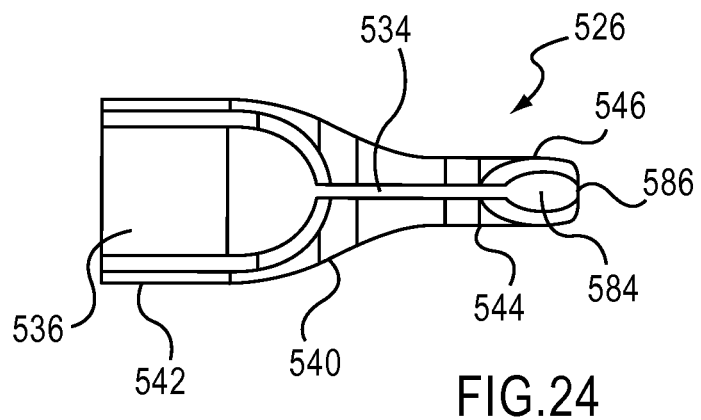
FIG. 24 is a top view of the tissue container of FIG. 23.

FIGS. 23 and 24 illustrate another embodiment of a tissue container 526. A tissue container 526 defines an interior region 532 configured to receive and contain a corneal tissue graft (not shown), and an elongated opening or slot 534 defined along a portion of a length of the tissue container 526 and in fluid communication with the interior region 532. The tissue container 526 also defines a side opening 536 at a proximal portion 542 of the tissue container 526 in fluid communication with the interior region 532. As described above, the side opening 536 can be used to insert a corneal tissue graft into the tissue container 526 and the elongate opening 534 allows fluid to flow into the interior region 532 of the tissue container 526 to irrigate a corneal tissue graft contained therein.

The tissue container 526 further includes a tapered or funnel portion 540 disposed between a proximal portion 542 and a cylindrical distal portion 544 of the tissue container 526. As with the previous embodiments, an angled distal end or tip portion 546 defines a distal opening 584. In this embodiment, a wall thickness at a distal end 586 of the tissue container 526 is thinner than a wall thickness of the remaining portion of the distal end portion 546. This configuration can further facilitate entry into an incision in a patient's eye.

Any combination of the components described herein can be provided in a kit to an eye bank, and/or to a surgeon. For example, in one embodiment, a can include a tissue container (e.g., 26, 126, 226, 526), an adaptor (e.g., 28, 128, 328), and an injector assembly (e.g., 24, 124, 424) configured to be matingly coupled to the adaptor and/or tissue container as described herein. The kit can be provided to, for example, an eye bank, that can preload a tissue graft as described above for medical device 120. The kit can optionally include a transport member (e.g., 30, 130, 230) or a transport member can be provided to or by the eye bank separately. The tissue container with the adaptor coupled thereto can be placed in a transport member as described above, and provided to a surgeon, along with the mating injector assembly as a kit. The same or different packaging can be used for the kit as provided to the eye bank and then to the surgeon.

The various components of the medical device (20, 120) can be formed with a variety of different materials known and used in medical devices, such as various stainless steels or polymer materials. The various components of the medical device (20, 120) can each be formed with various biocompatible metal materials, such as stainless steel, titanium, titanium alloy, surgical steel, metal alloys, or suitable biocompatible plastic materials, such as various polymers, or various flexible materials, various rubber materials, or combinations of various materials thereof. For example, the tissue container (26, 126, 226, 526), the adaptor (28, 128, 328) and the housing (158, 458) of an injector assembly (24, 124, 424) can each be formed with, for example, an acrylic polymer. The elongate member (157) of the plunger (156, 456) and the fluid port (176) can each be formed with, for example, a stainless steel, such as a 304 stainless steel or a suitable polymer material used in such medical applications. The plug element (172) can also be formed with, for example, an acrylic polymer, or other suitable polymers, plastic or metal materials.

Figure 25:
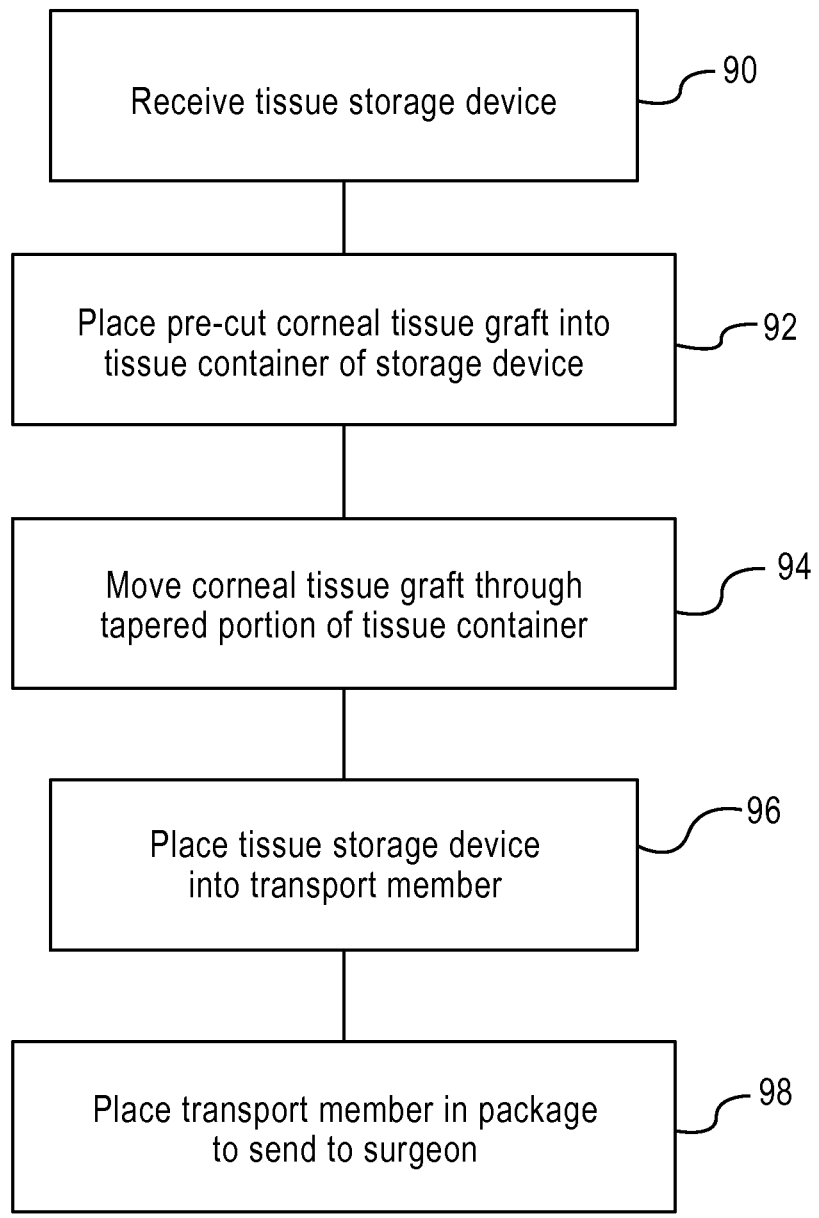
FIGS. 25 and 26 are each a flow chart illustrating a different embodiment of a method.

FIG. 25 is a flow chart illustrating a method of preparing and storing a corneal tissue graft within a medical device as described herein. At 90, at least a portion of a medical device (e.g., 20, 120, 220) is provided to a technician, at for example, an eye bank. For example, at least a tissue container (e.g., 26, 126, 226, 526) can be received. At 92, a technician at an eye bank places a precut corneal tissue graft into a tissue container (e.g., 26, 126, 226, 526) of the medical device. For example, the tissue graft is inserted through a side opening in the tissue container as described above.

After being positioned in the tissue container, at 94, the tissue graft is moved through a tapered portion of the tissue container, which induces the tissue graft to gently roll into a tubular or rolled form with the endothelium facing inside the rolled tissue (e.g., in the center). At 96, the tissue container can then be placed into a transport member (e.g., 30, 130, 230) containing a transplant storage medium, such as, for example, Optisol. As described above, in some embodiments, an adaptor (e.g., 28, 128, 328) can be coupled to the tissue container prior to inserting the tissue container in the transport member. At 98, the transport member is placed in a package to send to a surgeon or other medical professional. In some embodiments, the transport member can be placed in a package along with a mating injector assembly.

Figure 26:
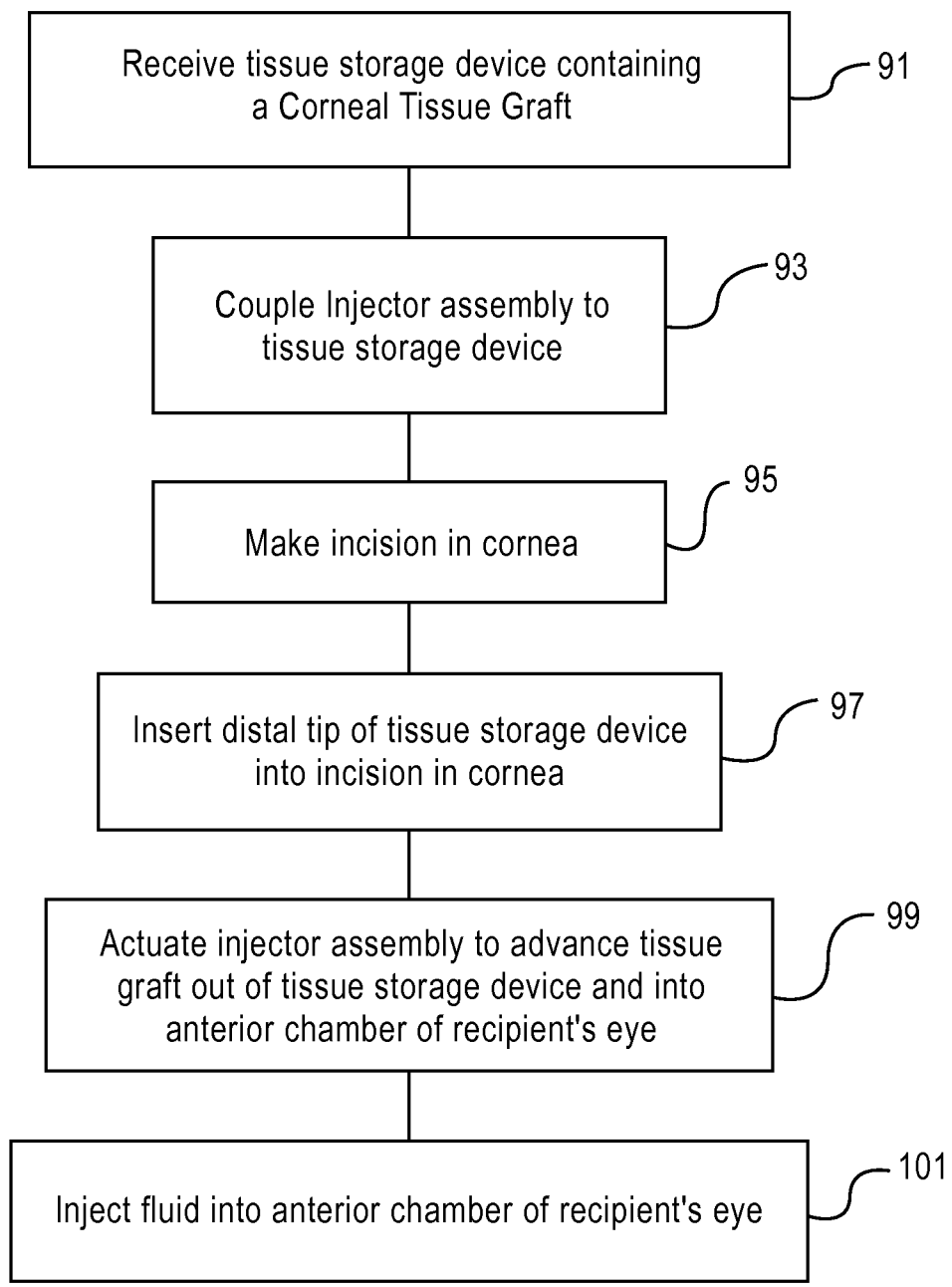

FIG. 26 is a flow chart illustrating an example method of receiving a corneal tissue graft and implanting the tissue graft into a patient's eye. At 91, a tissue storage device (e.g., 22, 122, 222) is received by a medical practitioner (e.g., surgeon). The tissue storage device includes a tissue container (e.g., 26, 126, 226, 526) with a corneal tissue graft disposed therein and an adaptor (e.g., 28, 128, 328) coupled to the tissue container. At 93, an injector assembly (e.g., 24, 124, 424) is coupled to the tissue storage device. In some embodiments, the injector assembly can be received in a kit with the tissue storage device. At 95, a small incision is made in the cornea of the intended recipient of the tissue graft. For example, the incision can be, 3 mm-4 mm in length. At 97, a distal end or tip of the tissue storage device is inserted into the incision in the cornea. At 99, the injector is actuated to gently advance the tissue graft out of the tissue storage container and into the anterior chamber of the recipient's eye. For example, the injector assembly can include a plunger configured to push the tissue graft out of the tissue container. At 101, a fluid (e.g., BSS) can be injected into the anterior chamber to help unroll the tissue graft. The fluid solution can be introduced, for example, via an integral irrigation channel of the injector assembly. For example, in some embodiments, an irrigation channel and port can be incorporated into the plunger of the injector assembly and a syringe can be used to inject the fluid into the injector assembly.

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

For example, although various embodiments have been described as having particular features and/or combinations of components, other embodiments are possible having any combination or sub-combination of any features and/or components from any of the embodiments described herein. For example, although the medical device 120 was shown and described with an adaptor 128, the adaptor 328 could alternatively be used with medical device 120. In addition, various combinations of components can be included in a kit, as described herein. The specific configurations of the various components can also be varied. For example, the size and specific shape of the various components can be different than the embodiments shown, while still providing the functions as described herein.

What is claimed is:

1. An apparatus, comprising:
   a tissue container defining an interior region, the interior region containing a precut corneal tissue graft in a rolled configuration,
   an adaptor including a distal portion and a proximal portion, wherein said distal portion defines an interior region having a first diameter and coupled to a proximal portion of the tissue container, and wherein said proximal portion of the adaptor defines a lumen having a second diameter, said first diameter being larger than the second diameter; and
   an injector assembly configured to be coupled to the adaptor and the tissue container, the injector assembly including a plunger configured to move within the adaptor and the tissue container to move the precut corneal tissue graft out of the interior region of the tissue container, the plunger defining an irrigation channel through which a fluid can be conveyed to the precut corneal tissue graft.

2. The apparatus of claim 1, wherein the adaptor is configured to prevent migration of the corneal tissue graft out of the interior region of the tissue container.

3. The apparatus of claim 1, further comprising:
   a transport member defining an interior chamber containing an optical transplant medium and configured to receive the tissue container and adaptor.

4. The apparatus of claim 1, wherein:
   the injector assembly is configured to move within the second diameter of the adaptor.

5. The apparatus of claim 1, wherein:
   the injector assembly includes a fitting in fluid communication with the irrigation channel, the fitting configured to be releasably coupled to a source of the fluid.

6. The apparatus of claim 1, wherein:
   the injector assembly is configured to be coupled to a syringe to communicate the fluid from the syringe to the irrigation channel.

7. The apparatus of claim 1, wherein the tissue container includes a tapered portion configured to induce the corneal tissue graft into the rolled configuration within the interior region of the tissue container.

8. The apparatus of claim 1, wherein the plunger has a distal end surface configured to contact the precut corneal tissue graft in the rolled configuration.

9. The apparatus of claim 1, wherein the plunger is configured to matingly engage a portion of a side wall that defines the interior region of the tissue container to move the precut corneal tissue graft.

10. The apparatus of claim 1, wherein the precut corneal tissue graft is in the rolled configuration such that an endothelial side of the corneal tissue graft is not in contact with an interior surface of the tissue container.

11. The apparatus of claim 1, wherein the tissue container includes a distal end portion and a tapered portion, the distal end portion having a first side wall defining a substantially constant inner diameter, the tapered portion disposed between the proximal portion of the tissue container and the distal end portion of the tissue container.

12. An apparatus, comprising:
   a tissue container including a proximal end portion, a cylindrical distal end portion having a first side wall defining a substantially constant inner diameter, and a tapered portion disposed therebetween, the cylindrical distal end portion containing a precut corneal tissue graft in a rolled configuration, a second side wall of the tissue container defining an opening at said proximal end portion, wherein said opening is in direct fluid communication with an interior region of the tissue container; and
   an injector assembly including a plunger, the plunger configured to matingly engage the first side wall to move the corneal tissue graft out of the tissue container and into an anterior chamber of a recipient's eye, the plunger defining an irrigation channel through which a fluid can be conveyed to the precut corneal tissue graft.

13. The apparatus of claim 12, further comprising:
an adaptor configured to be coupled to the tissue container, the adaptor configured to prevent the corneal tissue graft from migrating out of the tissue container.

14. The apparatus of claim 12, further comprising:
an adaptor configured to be coupled to the tissue container, the adaptor configured to be coupled to the injector assembly configured to move the corneal tissue graft out of the tissue container.

15. The apparatus of claim 12, further comprising:
an adaptor configured to be coupled to the tissue container, the adaptor includes a distal portion defining an interior region configured to receive the proximal end portion of the tissue container and a proximal portion defining a lumen configured to receive at least a portion of the injector assembly.

16. The apparatus of claim 12, further comprising:
a transport member defining an interior chamber containing an optical transplant medium and configured to receive the tissue container.

17. The apparatus of claim 12, wherein
the plunger of the injector assembly includes an end surface configured to contact the corneal tissue graft in the rolled configuration.

18. The apparatus of claim 12, wherein
the injector assembly is configured to be coupled to a syringe to communicate the fluid to an irrigation port of the injector assembly.

19. The apparatus of claim 12, wherein
a distal end portion of the plunger of the injector assembly includes a plug defining an opening through which the fluid can be conveyed to the corneal tissue graft.

20. The apparatus of claim 12, wherein the first side wall of the tissue container defines an elongated opening extending from said opening at the proximal end portion to the distal end portion and in fluid communication with the interior region of the tissue container such that a storage fluid can be communicated to the corneal tissue graft disposed within the tissue container.

21. An apparatus, comprising:
a tissue container defining an interior region containing a precut corneal tissue graft, the tissue container including a proximal end portion and a distal end portion, the distal end portion configured to maintain the precut corneal tissue graft within the interior region in a rolled configuration, a side wall of the tissue container defining an elongated opening extending along a length of the tissue container from the proximal end portion to the distal end portion and in direct fluid communication with the interior region of the tissue container such that a fluid can be communicated to the precut corneal tissue graft; and
an injector configured to move the precut corneal tissue graft out of the distal end portion of the tissue container, the injector having a distal end surface configured to contact the precut corneal tissue graft in the rolled configuration, the injector defining an irrigation channel through which an irrigation fluid can be conveyed to the precut corneal tissue graft.

22. The apparatus of claim 21, further comprising:
an adaptor configured to be coupled to the tissue container, the adaptor configured to prevent the corneal tissue graft from migrating out of the tissue container.

23. The apparatus of claim 21, further comprising:
an adaptor configured to be coupled to the tissue container and the injector.

24. The apparatus of claim 21, further comprising:
an adaptor configured to be coupled to the tissue container, the adaptor includes a distal portion and a proximal portion, the distal portion defining an interior region configured to receive the proximal end portion of the tissue container, the proximal portion defining a lumen configured to receive at least a portion of the injector.

25. The apparatus of claim 21, further comprising:
a transport member defining an interior chamber containing an optical transplant medium and configured to receive the tissue container.

26. The apparatus of claim 21, wherein:
a portion of the injector is configured to interface with the distal end portion of the tissue container such that the portion of the injector can move smoothly therethrough.

27. The apparatus of claim 21, wherein:
the injector includes a plug that defines at least a portion of the irrigation channel.

28. The apparatus of claim 21, wherein:
a proximal end portion of the injector includes a fitting configured to be coupled to a syringe to communicate the irrigation fluid to the irrigation channel.

29. An apparatus, comprising:
a tissue container defining an interior region, the tissue container including a proximal portion defining a first portion of the interior region, a cylindrical distal portion defining a second portion of the interior region, and a tapered portion disposed therebetween, the second portion of the interior region containing a precut corneal tissue graft in a rolled configuration; and
an injector assembly configured to be coupled to the tissue container, the injector assembly configured to move the corneal tissue graft out of the second portion of the interior region of the tissue container and into an anterior chamber of a recipient's eye, a plunger of the injector assembly defining an irrigation channel through which a fluid can be conveyed to the precut corneal tissue graft, the cylindrical distal portion of the tissue container including an angled tip, a wall thickness of a distal end portion of the angled tip being thinner than a wall thickness of the cylindrical distal portion of the tissue container, and wherein said cylindrical distal portion is formed from a non-flexible material.

30. The apparatus of claim 29, wherein the cylindrical distal portion is configured to matingly receive a portion of the injector assembly to move the precut corneal tissue graft.

31. The apparatus of claim 29, wherein the tapered portion is configured to induce the precut corneal tissue graft into the rolled configuration within the second portion of the interior region.

32. The apparatus of claim 29, wherein
the plunger is configured to move within the tissue container.

33. The apparatus of claim 29, wherein
the plunger of the injector assembly has an end surface configured to contact the corneal tissue graft in the rolled configuration.

34. The apparatus of claim 29, further comprising:
an adaptor configured to be coupled to the tissue container, the adaptor including a distal portion and a proximal portion, the distal portion of the adaptor defining an interior region configured to receive the proximal portion of the tissue container, the proximal portion of the adaptor defining a lumen configured to receive at least a portion of the injector assembly.

35. An apparatus, comprising:

a tissue container defining an interior region, the tissue container including a proximal end portion, a distal end portion, and a tapered portion disposed therebetween, the distal end portion of the interior region containing a precut corneal tissue graft therein in a rolled configuration;

an injector assembly configured to be coupled to the tissue container, the injector assembly configured to move the corneal tissue graft out of the interior region of the tissue container and into an anterior chamber of a recipient's eye, a plunger of the injector assembly defining an irrigation channel through which a fluid can be conveyed to the precut corneal tissue graft; and a transport member defining an interior chamber containing an optical transplant medium, the interior chamber configured to receive the tissue container therein.

36. The apparatus of claim 35, wherein:

a side wall of the tissue container defines an elongated opening configured to place the interior chamber in fluid communication with an interior region of the tissue container when the tissue container is within the interior chamber.

* * * * *